(12) United States Patent
Kim et al.

(10) Patent No.: US 7,262,313 B2
(45) Date of Patent: Aug. 28, 2007

(54) ORGANIC SILANE COMPOUND

(75) Inventors: Michael J. Kim, Daejeon (KR); Noma Kim, Daejeon (KR); Anna Lee, Daejeon (KR); Sera Kim, Daejeon (KR); Sukky Chang, Daejeon (KR); Sungchul Lim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 11/583,128

(22) Filed: Oct. 19, 2006

(65) Prior Publication Data

US 2007/0093671 A1    Apr. 26, 2007

(30) Foreign Application Priority Data

Oct. 20, 2005  (KR) ...................... 10-2005-0099190
Dec. 21, 2005  (KR) ...................... 10-2005-0127182

(51) Int. Cl.
   *C07F 7/02*  (2006.01)
(52) U.S. Cl. ...................... 556/415; 556/416; 556/428; 556/437; 556/438; 556/463; 556/465; 556/487
(58) Field of Classification Search ................ 556/415, 556/416, 428, 437, 438, 463, 465, 487
   See application file for complete search history.

(56) References Cited

U.S. PATENT DOCUMENTS 5,359,101 A * 10/1994 Woods et al. ................ 556/52

* cited by examiner

*Primary Examiner*—Elvis O. Price
(74) *Attorney, Agent, or Firm*—McKenna Long & Aldridge LLP

(57) ABSTRACT

The present invention relates to a novel organic silane compound, and more particularly, to a novel organic silane compound, useful in various applications, for the purpose of improving the affinity of an organic resin to an inorganic filler or improving the adhesion of a coating layer comprising matrix resin to a substrate. It is particularly useful for improving the adhesion of a polarizing plate adhesive for a liquid crystal display to a glass substrate, with little change over time even under hot and humid conditions.

8 Claims, No Drawings

ORGANIC SILANE COMPOUND

This application claims the benefit of the filing date of Korean Patent Application Nos. 10-2005-0099190 filed on Oct. 20, 2005 & 10-2005-0127182 filed on Dec. 21, 2005 in the Korean Intellectual Property Office, the disclosure of which is incorporated herein in its entirety by reference.

1. Technical Field

The present invention relates to a novel organic silane compound, and more particularly, to a novel organic silane compound useful in various applications for the purpose of improving the affinity of an organic resin to an inorganic filler or improving the adhesion of a coating layer comprising matrix resin to a substrate, particularly for improving the adhesion of a polarizing plate adhesive for a liquid crystal display to a glass substrate with little change over time, even under hot and humid conditions.

2. Background Art

Japanese Patent Laid-Open No. 3022993 discloses an adhesive composition comprising a silane compound having an epoxy group and Japanese Patent Laid-Open No. Hei 7-331204 discloses an adhesive composition comprising a silane compound having a hydrocarbon.

However, these adhesive compositions are disadvantageous in that they cannot offer adequate adhesion strength required under the actual situations where a substrate or a polarizing plate are used, the adhesion strength increases excessively under hot and humid conditions, or the adhesive may remain on the substrate after being peeled off.

DISCLOSURE OF THE INVENTION

An object of the present invention is to provide a novel organic silane compound, useful in various applications, for the purpose of improving the affinity of an organic resin to an inorganic filler or improving the adhesion of a coating layer comprising matrix resin to a substrate.

Another object of the present invention is to provide a novel organic silane compound which, when comprised in a polarizing plate adhesive for a liquid crystal display, improves adhesion to a glass substrate with little change over time, even under hot and humid conditions.

To attain the above objects, the present invention provides an organic silane compound represented by the following formula (1):

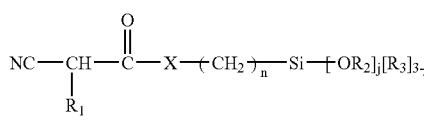

(1)

Wherein each of $R_1$, $R_2$ and $R_3$ is, independently, hydrogen or $C_1$-$C_3$ alkyl; X is —$NR_4$— (where $R_4$ is hydrogen or $C_1$-$C_3$ alkyl), oxygen or sulfur; n is an integer from 3 to 10; and j is an integer from 1 to 3.

Hereunder is given a detailed description of the present invention.

The present invention is characterized by a novel organic silane compound represented by the formula (1).

The organic silane compound represented by the formula (1) may be prepared by a one-step process or a two-step process.

In the one-step process for preparing the organic silane compound, 1-alkenyl cyanoacetate and trialkoxysilane may be reacted in the presence of chloroplatinic acid catalyst, Karstedt catalyst, or the complex of chloroplatinic acid and sym-divinyltetramethyldisiloxane, dichlorobis(triphenylphosphine) platinum (II), cis-dichlorobisacetonitrile platinum (II) or dicarbonyldichloro platinum (II). Preferably, the catalyst is selected from chloroplatinic acid or platinum-vinylsiloxane complex. Alternatively, the organic silane compound may be prepared by reacting cyanoacetyl chloride with N-alkylaminoalkyl trialkoxide in the presence of a tertiary amine.

The two-step process for preparing the organic silane compound is as follows: First, 1-alkenyl cyanoacetate and trichlorosilane are reacted in the presence of chloroplatinic acid catalyst or platinum-vinylsiloxane catalyst. Subsequently, methanolysis of the reaction product using methanol produces the novel organic silane compound.

The above reaction may be performed in a halogenated alkyl solvent such as chloroform, methylene chloride, dichloroethane, etc.; a cyclic ether solvent such as tetrahydrofuran, dioxin, etc.; or an aromatic organic solvent such as benzene, toluene, xylene, etc.

Preferably, the reaction is performed in the temperature range from 10 to 200° C., and more preferably from 50 to 150° C. Also, vacuum distillation may be performed for purification.

Most preferably, the substituent $R_1$ of the resultant organic silane compound represented by the formula (1) is hydrogen.

Specific examples of the silane compound of the present invention represented by the formula (1) include cyanoacetoxypropyl trimethoxysilane, which is represented by the following formula (2), and N-methyl-N-(3-trimethoxysilylpropyl)cyanoacetamide, which is represented by the following formula (3).

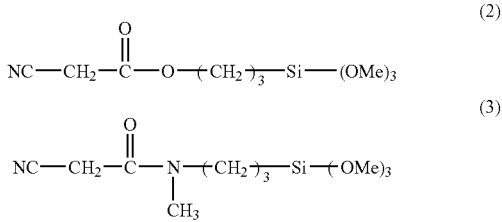

The organic silane compound represented by the formula (1) of the present invention is adequate for use in acrylic resin compositions, thermosetting resin compositions, thermoplastic resin compositions, etc.

The novel organic silane compound of the present invention represented by the formula (1) can be usefully used in matrix resins. In order to confirm the performance as an adhesion-promoting additive, an acrylic matrix resin was prepared using the organic silane compound of the present invention and its adhesion to glass was tested.

The acrylic matrix resin can be obtained from the copolymerization of a (meth)acrylic acid ester monomer having a $C_1$-$C_{12}$ alkyl group and a vinylic monomer having a hydroxy group.

For the (meth)acrylic acid ester monomer having a $C_1$-$C_{12}$ alkyl group, butyl (meth)acrylate, 2-ethylhexyl (meth)acrylate, ethyl (meth)acrylate, methyl (meth)acrylate, n-propyl (meth)acrylate, isopropyl (meth)acrylate, t-butyl (meth)acrylate, pentyl (meth)acrylate, n-octyl (meth)acrylate, isooctyl (meth)acrylate, isononyl (meth)acrylate, etc. may be used alone or in combination. And, for the vinylic monomer having a hydroxy group, 2-hydroxyethyl (meth)acrylate, 2-hydroxypropyl (meth)acrylate, 2-hydroxyethylene glycol (meth)acrylate, 2-hydroxypropylene glycol (meth)acrylate, etc. may be used.

In addition to the organic silane compound represented by the formula (1) and the acrylic matrix resin, a cross-linking agent may be used in the test. For the cross-linking agent, tolylene diisocyanate, diphenylmethane diisocyanate, hexamethylene diisocyanate, trimethylolpropane adduct of tolylene diisocyanate, etc. may be used.

Further, an additive selected from plasticizer, acrylic oligomer, emulsifier, birefringent low molecular weight compound, epoxy resin, hardener, UV stabilizer, antioxidant, colorant, modifier, filler, etc. may be added to the acrylic matrix resin as required.

BEST MODES FOR CARRYING OUT THE INVENTION

Practical and presently preferred embodiments of the present invention are illustrated as shown in the following examples. However, it will be appreciated that those skilled in the art may, in consideration of this disclosure, make modifications and improvements within the spirit and scope of the present invention.

EXAMPLES

Example 1

Synthesis of cyanoacetoxypropyltri methoxysilane [Formula (2)]

In a 1 L-reactor equipped with a thermometer and a condenser, 200 mL of THF, 40 g (0.319 mol) of alkyl cyanoacetate and 40 g (0.327 mol) of trimethoxysilane were added. After heating to 60° C., 0.05 g of chloroplatinic acid was added. After reaction for 4 hours, the solvent and unreacted reactants were removed. 73 g of cyanoacetoxypropyltrimethoxysilane [formula (2)] was obtained by vacuum distillation (yield: 91%).

The prepared cyanoacetoxypropyltrimethoxysilane was a colorless liquid. The results of NMR analysis are as follows:

$^1$H NMR (CDCl$_3$, 300 MHz): 0.70 (t, 2H), 1.83 (p, 2H), 3.50 (s, 2H), 3.61 (s, 9H), 4.22 (t, 2H)

$^{13}$C NMR (CDCl$_3$, 300 MHz): 4.6, 21.4, 24.0, 49.9, 67.9, 113.3, 163.1

Example 2

Synthesis of N-methyl-N-(3-trimethoxysilyl propyl)cyanoacetamide [Formula (3)]

In a 1 L-reactor equipped with a thermometer, a condenser and a dropping glass bottle, 200 mL of diethyl ether and 11 g (0.11 mol) of cyanoacetyl chloride were added. After stirring at room temperature in a nitrogen atmosphere, 20 g (0.104 mol) of N-methylaminopropylmethoxysilane and 11 g (0.14 mol) of pyridine dissolved in 100 mL of diethyl ether were slowly added to the reactor using a dropping funnel in 30 minutes. After stirring the reaction mixture for 2 hours at room temperature, the precipitated pyridinium salt, the solvent and unreacted reactants were removed. 21 g of N-methyl-N-(3-trimethoxysilylpropyl)cyanoacetamide [formula (3)] was obtained by vacuum distillation (yield: 75%).

The prepared N-methyl-N-(3-trimethoxysilylpropyl)cyanoacetamide was a colorless liquid. The results of NMR analysis are as follows:

$^1$H NMR (CDCl$_3$, 300 MHz): 0.65 (t, 2H), 1.28 (p, 2H), 2.97 (s, 3H), 3.37 (s, 9H), 3.47 (s, 9H), 3.55 (t, 2H)

$^{13}$C NMR (CDCl$_3$, 300 MHz): 3.54, 21.0, 24.95, 36.01, 48.57, 50.73, 115.19, 162.32

Example 3

Preparation of Acrylic Copolymer

In a 1,000 cc-reactor equipped with a nitrogen reflux unit and a cooler, a monomer mixture comprising 98 parts by weight of n-ethyl acrylate (EA) and 2 parts by weight of 2-hydroxyethyl methacrylate (2-HEMA) was added. Subsequently, 230 parts by weight of ethyl acetate (EAc) was added as a solvent. After purging with nitrogen gas for 20 minutes in order to remove oxygen, the reactor was maintained at 70° C. After homogenization, 0.03 part by weight of azobisisobutyronitrile (AIBN) diluted to 50% in ethyl acetate was added as a reaction initiator. After 7 hours of reaction, an acrylic copolymer having a molecular weight of 900,000 (measured using a polystyrene standard sample) was obtained.

Preparation of Acrylic Resin Composition

To 100 parts by weight of the acrylic copolymer prepared above were added 1.5 parts by weight of tolylene diisocyanate adduct of trimethylolpropane, as a polyfunctional isocyanate cross-linking agent, and 0.1 part by weight of cyanoacetoxypropyltrimethoxysilane [formula (2)] prepared in Example 1. The mixture was diluted properly, homogeneously mixed, coated on a releasing film, and dried to obtain an even acrylic resin layer layer having 30 micron of thickness. A polyester film (185 micron thickness) treated with corona was coated with the acrylic resin layer prepared above. The polyester film was cut into proper sizes for test (width 90 mm, length 170 mm).

Example 4

The procedure of Example 3 was repeated, except N-methyl-N-(3-trimethoxysilylpropyl)cyanoacetamide [formula (3)] prepared in Example 2 was used instead of cyanoacetoxypropyltrimethoxysilane [formula (2)] prepared in Example 1 during the preparation of the acrylic resin composition.

Comparative Example 1

The procedure of Example 3 was repeated, except cyanoacetoxypropyltrimethoxysilane [formula (2)] prepared in Example 1 was not added during the preparation of the acrylic resin composition.

Comparative Example 2

The procedure of Example 3 was repeated, except (3-glycidoxypropyl)trimethoxysilane was used, instead of cyanoacetoxypropyltrimethoxysilane [formula (2)] prepared in Example 1, during the preparation of the acrylic resin composition.

Measurement of Adhesion

Adhesion to glass was tested for the acrylic resin compositions prepared in Examples 3 and 4 and Comparative Examples 1 and 2 as follows:

PET films on which each of the acrylic resin compositions prepared in Examples 3 and 4 and Comparative Examples 1 and 2 were laminated with clean glass and kept at room temperature for 1 hour. Subsequently, they were kept under i) room temperature conditions (10 hours at room temperature), ii) dry conditions (10 hours at 60° C.) and iii) wet conditions (10 hours at 60° C. and R.H. 90%). Then, they were kept at room temperature for 2 hours. Adhesion to glass was tested at 300 mm/min and 180° peel adhesion, using a tensile testing machine. The results are given in Table 1 below.

TABLE 1

| | Adhesion to glass (g/25 mm) | | |
| --- | --- | --- | --- |
| Example | i) Room temperature condition | ii) Dry condition | iii) Wet condition |
| 3 | 610 | 720 | 790 |
| 4 | 580 | 760 | 810 |
| Comp. 1 | 110 | 150 | 120 |
| Comp. 2 | 260 | 450 | 470 |

As shown in Table 1, the acrylic resin compositions of Examples 3 and 4, in which the novel organic silane compound of the present invention represented by the formula (1) was used, showed superior adhesion strength to glass compared with those of Comparative Examples 1 and 2 under room temperature conditions, dry conditions and wet conditions.

INDUSTRIAL APPLICABILITY

As apparent from the above description, the novel organic silane compound in accordance with the present invention is useful in various applications for the purpose of improving the affinity of an organic resin to an inorganic filler or improving the adhesion of a coating layer comprising matrix resin to a substrate. Particularly, it is useful for improving the adhesion of a polarizing plate adhesive for a liquid crystal display to a glass substrate with little change over time even under hot and humid conditions.

Those skilled in the art will appreciate that the concepts and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the present invention as set forth in the appended claims.

What is claimed is:

1. An organic silane compound represented by the following formula (1):

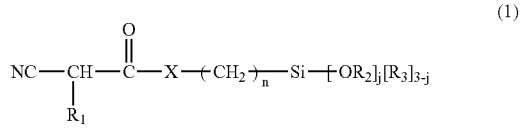

Wherein each of $R_1$, $R_2$ and $R_3$ is, independently, hydrogen or $C_1$-$C_3$ alkyl; X is —$NR_4$— (where $R_4$ is hydrogen or $C_1$-$C_3$ alkyl), oxygen or sulfur; n is an integer from 3 to 10; and j is an integer from 1 to 3.

2. The organic silane compound represented by the formula (1) as set forth in claim 1, which is prepared by reacting 1-alkenyl cyanoacetate and trialkoxysilane in the presence of chloroplatinic acid catalyst or platinum-vinyl-siloxane catalyst.

3. The organic silane compound represented by the formula (1) as set forth in claim 1, which is prepared by reacting 1-alkenyl cyanoacetate and trichlorosilane in the presence of chloroplatinic acid catalyst or platinum-vinyl-siloxane catalyst, and performing methanolysis.

4. The organic silane compound represented by the formula (1) as set forth in claim 1, which is prepared by reacting 1-alkenyl cyanoacetate and trialkoxysilane in the presence of chloroplatinic acid catalyst.

5. The organic silane compound represented by the formula (1) as set forth in claim 1, which is prepared by reacting cyanoacetyl chloride and N-alkylaminoalkyl trialkoxide in the presence of a tertiary amine.

6. The organic silane compound represented by the formula (1) as set forth in claim 1, wherein the substituent $R_1$ in the formula (1) is hydrogen.

7. The organic silane compound represented by the formula (1) as set forth in claim 1, which is cyanoacetoxypropyltrimethoxysilane represented by the following formula (2) or N-methyl-N-(3-trimethoxysilylpropyl)cyanoacetamide represented by the following formula (3):

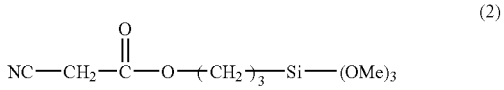

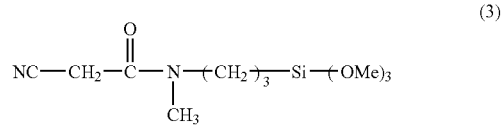

8. The organic silane compound represented by the formula (1) as set forth in claim 1, which is used in an acrylic resin composition, a thermosetting resin composition or a thermoplastic resin composition.

* * * * *